United States Patent
Zemach et al.

(10) Patent No.: US 11,395,470 B1
(45) Date of Patent: Jul. 26, 2022

(54) SESAME WITH HIGH OIL CONTENT AND/OR HIGH YIELD

(71) Applicant: EQUI-nom Ltd., Givat Brenner (IL)

(72) Inventors: Itay Zemach, Rehovot (IL);
Menachem Sklarz, Beer Sheva (IL);
Oswald Crasta, Lubbock, TX (US)

(73) Assignee: EQUI-NOM LTD., Givat Brenner (IL)

( * ) Notice: Subject to any disclaimer, the term of this patent is extended or adjusted under 35 U.S.C. 154(b) by 0 days.

(21) Appl. No.: 17/474,944

(22) Filed: Sep. 14, 2021

(51) Int. Cl.
*A01H 5/10* (2018.01)
*A01H 6/66* (2018.01)

(52) U.S. Cl.
CPC ............. *A01H 6/66* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,426,039 A | 6/1995 | Wallace et al. | |
| 5,468,613 A | 11/1995 | Erlich et al. | |
| 5,492,547 A | 2/1996 | Johnson | |
| 5,565,350 A | 10/1996 | Kmiec | |
| 5,981,832 A | 11/1999 | Johnson | |
| 6,100,452 A | 8/2000 | Langham | |
| 6,455,758 B1 | 9/2002 | Johnson | |
| 6,670,524 B1 | 12/2003 | Potter et al. | |
| 7,250,552 B2 | 7/2007 | Han et al. | |
| 7,847,149 B2 | 12/2010 | Langham | |
| 8,058,503 B1 | 11/2011 | Langham | |
| 8,080,707 B2 | 12/2011 | Langham | |
| 8,581,028 B2 * | 11/2013 | Langham | A01H 6/66 800/266 |
| 8,637,729 B2 | 1/2014 | Foncelle et al. | |
| 8,656,692 B2 | 2/2014 | Langham | |
| 8,664,472 B2 | 3/2014 | Langham | |
| 8,692,064 B2 | 4/2014 | Nguyen et al. | |
| 8,779,233 B1 | 7/2014 | Schnable et al. | |
| 8,987,549 B2 | 3/2015 | Baxter et al. | |
| 8,993,835 B2 | 3/2015 | Langham | |
| 9,000,258 B2 | 4/2015 | Ligthart et al. | |
| 9,125,372 B1 | 9/2015 | Langham | |
| 9,144,220 B1 | 9/2015 | Langham | |
| 9,167,795 B2 | 10/2015 | Langham | |
| 9,462,820 B2 | 10/2016 | Tadaki | |
| 9,485,936 B2 | 11/2016 | Page | |
| 10,577,623 B2 * | 3/2020 | Gar | A01H 6/66 |
| 11,044,884 B1 * | 6/2021 | Zemach | A01H 5/10 |
| 2003/0208798 A1 | 11/2003 | Langham | |
| 2009/0235394 A1 | 9/2009 | Langham | |
| 2011/0154528 A1 | 6/2011 | Ragot et al. | |
| 2011/0271360 A1 | 11/2011 | Langham | |
| 2014/0215657 A1 | 7/2014 | Nguyen et al. | |
| 2015/0082476 A1 | 3/2015 | Baxter et al. | |
| 2015/0101073 A1 | 4/2015 | Brugmans et al. | |
| 2015/0150155 A1 | 5/2015 | Black et al. | |
| 2017/0055481 A1 | 3/2017 | Brugmans et al. | |
| 2020/0093087 A1 | 3/2020 | Gar et al. | |
| 2021/0307285 A1 | 10/2021 | Tollman | |
| 2022/0010325 A1 | 1/2022 | Gar | |

FOREIGN PATENT DOCUMENTS

| | | |
|---|---|---|
| CN | 106337086 B | 6/2017 |
| IL | 239702 | 6/2015 |
| WO | WO 93/22443 | 11/1993 |
| WO | WO 2017/103928 | 6/2017 |
| WO | WO 2018/211496 A1 | 11/2018 |
| WO | WO 2020/093065 | 5/2020 |
| WO | WO 2020/093065 A1 | 5/2020 |

OTHER PUBLICATIONS

Zhang et a. Genome Biology(2013),14:401.*
Uzun et al. Plant Breeding (2003)122:95-97.*
Wei et al. BMC Genomics (2011),12:451.*
Ashri A. Sesame Breeding. In: Janick J. (ed.), Plant Breeding Reviews vol. 16. John Wiley and Sons, Somerset, NJ, pp. 179-228 (1998).
Wu et al.; High-Density Genetic Map Construction and QTLs Analysis of Grain Yield-Related Traits in Sesame (*Sesamum indicum* L.) Based on RAD-Seq Technology, BMC Plant Biology 14: 274 (2014).
Office Action dated Jan. 1, 2021 for related U.S. Appl. No. 17/076,027.
Notice of Allowance dated Apr. 7, 2021 for related U.S. Appl. No. 17/076,027.
Wang et al. "Genome sequencing of the high oil crop sesame provides insight into oil biosynthesis" *Genome Biology*, 15:R39, Feb. 27, 2014.
Lander ES and Botstein D. "Mapping mendelian factors underlying quantitative traits using RFLP linkage maps" Genetics. Jan. 1989 ;121(1):pp. 185-199.

(Continued)

*Primary Examiner* — Medina A Ibrahim
(74) *Attorney, Agent, or Firm* — Pearl Cohen Zedek Latzer Baratz LLP (57) ABSTRACT

Sesame plants with high oil content and/or high yield, and parts thereof are provided. Phenotypic and genotypic analysis of many sesame varieties were performed to derive markers for phenotypic traits that contribute to high oil content and/or high yield, and a breeding simulation was used to identify the most common and most stable markers. Examples for such phenotypic traits include the oil content as measured by near infrared spectroscopy, and yield traits related to plant morphology, number of capsules and the size of the seeds. Following verification of trait stability over several generations, markers and marker cassettes were defined as being uniquely present in the developed sesame lines. The resulting high oil content and/or high yield, shatter-resistant sesame lines can be used to increase sesame oil production for its various uses.

10 Claims, 4 Drawing Sheets

Specification includes a Sequence Listing.

(56) References Cited

OTHER PUBLICATIONS

Haley CS and Knott SA. "A simple regression method for mapping quantitative trait loci in line crosses using flanking markers" Heredity (Edlnb). Oct. 1992;69(4):pp. 315-324.
Jansen, R.C. "Controlling the type I and type II errors in mapping quantitative trait loci" Genetics 138, 1994, pp. 871-881.
Kwoh et al. "Transcription-based amplification system and detection of amplified human immunodeliciency virus type 1 with a bead-based sandwich hybridization format" Proc Natl Acad Sci U S A. Feb. 1989;86(4)pp. 1173-1177.
J.C. Guatelli et al. "Isothermal, in vitro amplification of nucleic acids by a multienzyme reaction modeled after retroviral replication" Proc Natl Acad Sci U S A. Mar. 1990; 87(5): pp. 1874-1878.
Lomeli H. et al. "Quantitative assays based on the use of replicatable hybridization probes" Clinical Chemistry Sep. 1989, 35 (9) pp. 1826-1831.
Landegren U. et al. "A ligase-mediated gene detection technique" Science. Aug. 26, 1988;241(4869):pp. 1077-1080.
Vos P. et al. "AFLP: a new technique for DNA fingerprinting" Nucleic Acids Res. Nov. 11, 1995;23(21):pp. 4407-4414.
Lincoln, S., Daly, M. & Lander, E.S. "Mapping genes controlling quantitative traits with MAPMAKER/QTL 1.1," in Whitehead Institute Technical Report vol. 2, Whitehead Institute, Cambridge, Massachusetts, 1994.
Yefim Ronin et al. "Building reliable genetic maps: different mapping strategies may result in different maps" Natural Science, vol. 2, Issue 6, Jun. 2010, pp. 576-589.
Korol A.B. et al. "Enhanced efticiency of quantitative trait loci mapping analysis based on multivariate complexes of quantitative traits" Genetics, Apr. 2001; 157(4): pp. 1789-1803.
L Kruglyak and E S Lander "A nonparametric approach for mapping quantitative trait loci" Genetics Mar. 1, 1995 vol. 139 No. 3, pp. 1421-1428.
Jansen RC and Stam P. "High resolution of quantitative traits into multiple loci via interval mapping" Genetics. Apr. 1994:136(4):pp. 1447-1455.
Zeng ZB "Precision mapping of quantitative trait loci" Genetics.;136(4), Apr. 1994; pp. 1457-1468.
Utz and Melchinger "Biometrics in Plant Breeding", van Oijen, Jansen (eds.) Proceedings of the Ninth Meeting of the Eucarpia Section Biometrics in Plant Breeding, The Netherlands, 1994, pp. 195-204.
R.S. Reiter el al. "Global and local genome mapping in *Arabidopsis thaliana* by using recombinant inbred lines arid random amplified polymorphic DNAs" Proc Natl Acad Sci U S A., Feb. 15, 1992; 89(4): pp. 1477-1481.
Ashri A. & Singh R.J "Chromosome Engineering and Crop Improvement" Sesame (*Seamum indicum* L.) Genetic Resources Oilseed Crops, 4, 2007, pp. 231-280.
Singh et al. "Unlocking the Potential of Genetic Resources for Improvement of Sesame (*Sesamum indicum* L.): The Current Scenario" Gene Pool Diversity and Crop Improvement; vol. 1, Chapter 15, Feb. 2016, pp. 447-479.
Wang et al. "Updated sesame genome assembly and fine mapping of plant height and seed coat color QTLs using a new high-density genetic map" BMC Genomics. 5;17:31 , Jan. 2016.
International Search Report and Written Opinion dated Jul. 22, 2018 for PCT Application No. PCT/IL2018/050520.

Notice of Allowance dated Oct. 17, 2019 for related U.S. Appl. No. 16/109,346, U.S. Pat. No. 10,577,623, issued Mar. 3, 2020.
Dan Mirjafarov; An alterative to GMOs: how to design plants without interfering with the genome; Sep. 14, 2016, retrieved from the Internet: https://agravery.com/uk/posts/show/alternative-gmo-ak-mozna-konstruuvati-roslini-ne-vtrucaucis-v-genom.
Uzin B et al; Identificationof a molecular marker linked to the closed capsule mutant trait in sesame using AFLP; Plant Breeding, Paul Parey Scientific Publ, Berlin, DE, vol. 122, No. 1, Feb. 1, 2003, pp. 95-97.
Search Report dated Nov. 24, 2020 for related European Application No. EP18802371.7.
Zhang et al; Construction of a high-density genetic map for sesame based on large scale marker development by specific length amplified fragment (SLAF) sequencing: BMC Plant Biology, 2013, 13:141.
Office Action dated Apr. 4, 2019 for related U.S. Appl. No. 16/109,346.
Office Action dated Aug. 21, 2019 for related U.S. Appl. No. 16/109,346.
Notice of Allowance dated Jul. 29, 2021 for related U.S. Appl. No. 16/706,752.
Office Action dated Feb. 16, 2021 for related U.S. Appl. No. 16/706,752.
International Preliminary Report on Patentability dated Nov. 19, 2019 for related PCT Application No. PCT/CZ2018/050520.
Yol, Engin et al., "A High-Density SNP Genetic Map Construction Using ddRAD-Seq and Mapping of Capsule Shattering Trait in Sesame," Frontiers in Plant Science (2021) 12: 1-13.
Zhang Haiyang, et al., "Genetic Analysis and QTL Mapping of Seed Coat Color in Sesame (*Sesamum indicum* L.)," PLoS ONE, May 21, 2013, vol. 8, No. 5, pp. e63898, abstract, p. 2, col. 1, para. 2, accessed Jan. 19, 2022 at https//journals.plos.org/plosone/article?id=10.1371/journal.pone.0063898.
GenBank JP649882 TSA (*Sesamum indicum* Locus_18970_Transcript_2/2_Confidence_0.8757_Length_628 mRNA sequence) Jul. 30, 2012 (retrieved Mar. 18, 2020). Retrieved from the internet <URL: https://www.ncbi.nim.nih.gov/nuccore/JP649882.1/ > whole doc.
GenBank JL343152 "TSA: Sesamum indicum cultivar Zhongzhi 11 Unigene21112 mRNA sequence") May 31, 2016 (retrieved Mar. 18, 2020). Retrieved from the internet <URL: https://www.ncbi.nim.nih.gov/nuccore/JL343152 > whole doc.
International Search Report and Written Opinion dated Apr. 6, 2020 for International Application No. PCT/US2019/059725.
International Preliminary Report on Patentability dated Apr. 27, 2021 for International Application No. PCT/US2019/059725.
Office Action dated Dec. 6, 2021 in U.S. Appl. No. 16/706,752.
European Search Report and Annex dated Mar. 18, 2022 for European Application No. 21204027.3.
Zhou, Rong, et al. "Genome-Wide Association Studies of 39 Seed Yield-Related Traits in Sesame (*Sesamum indicum* L.)," International Journal of Molecular Sciences 19.9 (Sep. 17, 2018): 2794.
Zhang, Haiyang et al., "TSA: Sesamum indicum Locus_1371_Transcript_1/1_Confidence_1.000_Length_2240 mRNA Sequence", XP055899043, Database accession No. EM_TSA:JP632997 (Jul. 31, 2012).
Zhang, Haiyang et al; Development and Validation of Genic-SSR Markers in Sesame by RNA-seq; BMC Genomics, Biomed Central Ltd, London, UK, vol. 13, No. 1, Jul. 16, 2012.
Wei, Wenliang et al., "TSA: Sesamum indicum Cultivar Zhongzhi 11 Unigene2486mRNA Sequence", XP055899141, Database accession No. EM_TSA:JL323849 (Oct. 2, 2011).

\* cited by examiner

```
SEQUENCE LISTING

<160> NUMBER OF SEQ ID NOS: 18

<210> SEQ ID NO 1
<211> LENGTH: 201
<212> TYPE: DNA
<213> ORGANISM: Sesamum indicum

<400> SEQUENCE: 1
tttacctaat gaggtacaag tctgaggcct ttggaaggtt caaggagtac agacttgaag      60
tcaagaatca aactagccgt aaattaaaac ccttcgatca aactgaggca gagagtattt    120
aagtggtgaa tttgttgatt acttaaaaga gaatggaatt ctcactcaat ggactcctct    180
tgaacgccat aacttaatag c                                              201

<210> SEQ ID NO 2
<211> LENGTH: 201
<212> TYPE: DNA
<213> ORGANISM: Sesamum indicum

<400> SEQUENCE: 2
tttacctaat gaggtacaag tctgaggcct ttggaaggtt caaggagtac agacttgaag      60
tcaagaatca aactagccgt aaattaaaac ccttcgatca gactgaggca gagagtattt    120
aagtggtgaa tttgttgatt acttaaaaga gaatggaatt ctcactcaat ggactcctct    180
tgaacgccat aacttaatag c                                              201

<210> SEQ ID NO 3
<211> LENGTH: 201
<212> TYPE: DNA
<213> ORGANISM: Sesamum indicum

<400> SEQUENCE: 3
ctaagtcagt tcttttcatt atacacggaa tgggcactgg agttttgaag gagcgtgtgc      60
ttgaactact aagaaaccat ccacgcattg caaagtttga acaggaaagc ccaatgaatt    120
atggttgtac agtagcctat atcaagtgaa cgtgtgattg tatcagctat caagaaggca    180
gtgatattct ttgaattttg t                                              201

<210> SEQ ID NO 4
<211> LENGTH: 201
<212> TYPE: DNA
<213> ORGANISM: Sesamum indicum

<400> SEQUENCE: 4
ctaagtcagt tcttttcatt atacacggaa tgggcactgg agttttgaag gagcgtgtgc      60
ttgaactact aagaaaccat ccacgcattg caaagtttga tcaggaaagc ccaatgaatt    120
atggttgtac agtagcctat atcaagtgaa cgtgtgattg tatcagctat caagaaggca    180
gtgatattct ttgaattttg t                                              201
```

<210> SEQ ID NO 5
<211> LENGTH: 201
<212> TYPE: DNA
<213> ORGANISM: Sesamum indicum

<400> SEQUENCE: 5

```
cgttaacaga gagtgtatga ggatgctgtc tcggagggaa atcccaagaa atatagtgca      60
tgtcatggtt gacaacggtt gggacaaact ctggagcatt acagataaca gtctggaaat    120
agccttctgg ggaggaaacg aagtttgagt agtacatgag aagggttctt gggagattat    180
cccaacccca tatgcagtac t                                               201
```

<210> SEQ ID NO 6
<211> LENGTH: 201
<212> TYPE: DNA
<213> ORGANISM: Sesamum indicum

<400> SEQUENCE: 6

```
cgttaacaga gagtgtatga ggatgctgtc tcggagggaa atcccaagaa atatagtgca      60
tgtcatggtt gacaacggtt gggacaaact ctggagcatt gcagataaca gtctggaaat    120
agccttctgg ggaggaaacg aagtttgagt agtacatgag aagggttctt gggagattat    180
cccaacccca tatgcagtac t                                               201
```

<210> SEQ ID NO 7
<211> LENGTH: 160
<212> TYPE: DNA
<213> ORGANISM: Sesamum indicum

<400> SEQUENCE: 7

```
gcactgcaac gctggactca agtttcaaca cctcaacacc cccatactca gtgtaagtcc      60
aggccttcat ctctgatgga atggaagaag aactcttgtt agaggcggtc tcagcagaag    120
gagcagaagt tgcaaatact ctgagaggtt gagggccaaa                           160
```

<210> SEQ ID NO 8
<211> LENGTH: 160
<212> TYPE: DNA
<213> ORGANISM: Sesamum indicum

<400> SEQUENCE: 8

```
gcactgcaac gctggactca agtttcaaca cctcaacacc cccatactca gtgtaagtcc      60
aggccttcat ctctgatggg atggaagaag aactcttgtt agaggcggtc tcagcagaag    120
gagcagaagt tgcaaatact ctgagaggtt gagggccaaa                           160
```

<210> SEQ ID NO 9
<211> LENGTH: 201
<212> TYPE: DNA
<213> ORGANISM: Sesamum indicum

<400> SEQUENCE: 9

```
tatacttgcc atatgattga ttcaaatttg atcgagtcga gtctgaatta aattttttca      60
tattttaag ggatgattcg gctagataag acaattttc caaaccaaat gaaattcacc      120
gcttaactat tttcatcttt gatcaaatta aagagtttcc actacttcgt tgatctaatt    180
ttgggttaaa tacagtttac t                                               201
```

<210> SEQ ID NO 10
<211> LENGTH: 201

```
<212> TYPE: DNA
<213> ORGANISM: Sesamum indicum

<400> SEQUENCE: 10
tatacttgcc atatgattga ttcaaatttg atcgagtcga gtctgaatta taattttttca    60 tattttttaag ggatgattcg gctagataag acaattttttc taaaccaaat gaaattcacc   120
gcttaactat tttcatcttt gatcaaatta aagagtttcc actacttcgt tgatctaatt    180
ttgggttaaa tacagtttac t                                              201

<210> SEQ ID NO 11
<211> LENGTH: 201
<212> TYPE: DNA
<213> ORGANISM: Sesamum indicum

<400> SEQUENCE: 11
gggctcatct gatcatgtac acacaaatac tatgtaccac tgcggaacat ttttttgtcct    60 atgacttagg gccttttttac ttttggttcc attggttatg aaattttttcaa ttttttggtcca  120 ataactttaa aaaatagca cttttggccc gtgacatatt ttcattagat atttaaagca    180
aaagaccacg tgtggccgtt a                                              201

<210> SEQ ID NO 12
<211> LENGTH: 201
<212> TYPE: DNA
<213> ORGANISM: Sesamum indicum

<400> SEQUENCE: 12
gggctcatct gatcatgtac acacaaatac tatgtaccac tgcggaacat ttttttgtcct    60 atgacttagg gccttttttac ttttggttcc attggttatg gaattttttcaa ttttttggtcca  120 ataactttaa aaaatagca cttttggccc gtgacatatt ttcattagat atttaaagca    180
aaagaccacg tgtggccgtt a                                              201

<210> SEQ ID NO 13
<211> LENGTH: 201
<212> TYPE: DNA
<213> ORGANISM: Sesamum indicum

<400> SEQUENCE: 13
ctgtttgatt agaaagctgg atcatgttgt gcaaataaca attttctatt ccagaatact     60
actgcaggct gtgggactcg ctgattttgg ctcaagaaat agtcaataat catttacttg    120
aagcataatt actccaagaa ttttaggatt gtatatttcg tgaattcgaa caagaattgc    180
ccgtgaccag ttgccatctg a                                              201

<210> SEQ ID NO 14
<211> LENGTH: 201
<212> TYPE: DNA
<213> ORGANISM: Sesamum indicum

<400> SEQUENCE: 14
ctgtttgatt agaaagctgg atcatgttgt gcaaataaca attttctatt ccagaatact     60
actgcaggct gtgggactcg ctgattttgg ctcaagaaat tgtcaataat catttacttg    120
aagcataatt actccaagaa ttttaggatt gtatatttcg tgaattcgaa caagaattgc    180
ccgtgaccag ttgccatctg a                                              201

<210> SEQ ID NO 15
```

```
<211> LENGTH: 201
<212> TYPE: DNA
<213> ORGANISM: Sesamum indicum

<400> SEQUENCE: 15
atcatgaatt ttactcctat tttttttgtta atattaacaa atctagtgga ttttgactaa      60
caaagggact tattttatta aacgaaagca accttcaagg atattaaata taatttttca     120
aaccacatga gatttatatg caattacatt aaatttcggt agagtggagt agttatccct     180
agaaatatta cagtcgaagt g                                               201

<210> SEQ ID NO 16
<211> LENGTH: 201
<212> TYPE: DNA
<213> ORGANISM: Sesamum indicum

<400> SEQUENCE: 16
atcatgaatt ttactcctat tttttttgtta atattaacaa atctagtgga ttttgactaa      60
caaagggact tattttatta aacgaaagca accttcaagg gtattaaata taatttttca     120
aaccacatga gatttatatg caattacatt aaatttcggt agagtggagt agttatccct     180
agaaatatta cagtcgaagt g                                               201

<210> SEQ ID NO 17
<211> LENGTH: 201
<212> TYPE: DNA
<213> ORGANISM: Sesamum indicum

<400> SEQUENCE: 17
tatttattac ttgtatttct tcttgattag ctcgcaagat tggaagggac gactaaaatt      60
accaccagca gacactcgtt atagaaccga ggtaagtttc ctgtaatatg ccagtttgtg    120
aactggttgt tgaaacaaac atctttatta ttatttttat ttgcctttca ggatgttaca    180
gctaccaaag gaaatgaatt t                                              201

<210> SEQ ID NO 18
<211> LENGTH: 201
<212> TYPE: DNA
<213> ORGANISM: Sesamum indicum

<400> SEQUENCE: 18
tatttattac ttgtatttct tcttgattag ctcgcaagat tggaagggac gactaaaatt      60
accaccagca gacactcgtt atagaaccga ggtaagtttc ttgtaatatg ccagtttgtg    120
aactggttgt tgaaacaaac atctttatta ttatttttat ttgcctttca ggatgttaca    180
gctaccaaag gaaatgaatt t                                              201
```

SESAME WITH HIGH OIL CONTENT AND/OR HIGH YIELD

SEQUENCE LISTING

The instant application contains a Sequence Listing which has been submitted electronically in ASCII format and is hereby incorporated by reference in its entirety. Said ASCII copy, created on Sep. 1, 2021, is named P-606512-US_ST25.txt and is 7,040 bytes in size.

BACKGROUND OF THE INVENTION

1. Technical Field

The present invention relates to the field of sesame genetics and breeding, and more particularly, to quantitative trait loci (QTLs, or QTL) associated with sesame oil content and crop yield.

2. Discussion of Related Art

Sesame (*Sesamum indicum*) is an oilseed crop that is cultivated over a large range of soil and climate conditions, typically in subtropical climates, and is used for seeds, oil and paste products. Low yield varieties are commonly used, yet such varieties make sesame non-profitable to grow in developed countries.

U.S. Pat. No. 10,577,623, which is incorporated herein by reference in its entirety, discloses genetic improvement for shatter resistant capsules, and more specifically, novel QTL conferring shatter resistant capsules, and methods for introgressing the novel QTL into elite germplasm in a breeding program for shatter resistant capsules.

SUMMARY OF THE INVENTION

The following is a simplified summary providing an initial understanding of the invention. The summary does not necessarily identify key elements nor limit the scope of the invention, but merely serves as an introduction to the following description.

One aspect of the present invention provides a high oil and/or high yield sesame plant with shatter-resistant capsules, progeny thereof and/or part(s) thereof, the sesame plant comprising: a plurality of quantitative trait loci (QTLs) having a corresponding plurality of nucleic acid genetic markers that are associated with a plurality of phenotypic traits of the sesame plant comprising at least an oil level trait and a yield trait, wherein the QTLs are combined in the sesame plant from a plurality of sesame varieties by computationally supported breeding, wherein the QTLs comprise QTL 1 associated with high oil content, with corresponding markers set forth in SEQ ID NOs 1 or 2, wherein the sesame plant or part thereof is homozygous with respect to SEQ ID NO 1, and wherein the sesame plant further comprises at least one of: QTLs 2, 3 and/or QTLs 2, 3, 4, 5 and/or QTLs 2, 3, 4, 5, 7 and/or QTLs 3, 8, 9 and/or QTLs 3, 4, 6, 8, 9.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout. In the accompanying drawings.

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention may be practiced without the specific details presented herein. Furthermore, well known features may have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that may be practiced or carried out in various ways as well as to combinations of the disclosed embodiments. Also, it is to be understood that the phraseology and terminology employed herein are for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing". "deriving" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Sesame plants and parts thereof are provided, which produce higher oil content and/or higher yield than current varieties. Phenotypic and genotypic analyses of many sesame varieties were performed to derive markers for high oil and/or high yield and other related phenotypic traits, and a breeding simulation was used to identify the most common and most stable markers. Following verification of trait stability over several generations, markers and marker cassettes were defined as being uniquely present in the developed sesame lines. The resulting high oil and/or high yield sesame lines may be used to increase the oil content, oil composition and yield of sesame crops for their various uses.

U.S. Pat. No. 10,577,623 and U.S. Patent Application Publication No. 2020/0093087 teach QTLs that confer shatter resistant capsules, and elite sesame varieties having shatter resistant capsules. Shatter resistant lines were used at least partly to further derive the disclosed high oil and/or high yield sesame lines disclosed herein.

Shatter resistant capsules were characterized in fully developed capsules having at most 10% seed moisture, and the shatter-resistant capsules were characterized by at least one of the features: (i) at least 80% seed retention after shaking the plant. (ii) at least 80% seed retention after the capsules are turned upside down, (iii) a ratio of at least 5:1 between a total length of the capsule and a length of a zone in which the capsule tips are open, and/or 20-30% of the capsules retain 90-95% of the seeds in fully developed green capsules before drying.

Various embodiments comprise high yield sesame plants with shatter-resistant capsules, or part(s) thereof, that comprise a plurality of loci associated with a corresponding plurality quantitative trait loci (QTLs) having a corresponding plurality of nucleic acid genetic markers that are associated with a plurality of phenotypic traits of the sesame plant. The QTLs are combined in the sesame plants from a plurality of sesame varieties according to computationally supported breeding tools. Phenotypic and genotypic analyses of many sesame varieties were performed to derive markers for phenotypic traits that contribute to high oil and/or high yield, and a breeding simulation was used to identify the most common and most stable markers. Examples of such phenotypic traits include the oil content as measured by near infrared spectroscopy, and yield traits such as the number of capsules on lateral shoots, the branching width, the plant total height, the average length of the seeds and the number of capsules on the main stem. Following verification of trait stability over several generations, markers and marker cassettes were defined as being uniquely present in the developed sesame lines. The resulting high oil and/or high yield sesame lines can be used to increase sesame oil quantity, oil quality and yield for its various uses. Details concerning the QTLs and markers are provided in Table 1 below, and the methods used to develop and select the varieties are disclosed with respect to FIG. 2 below.

It is noted that disclosed high oil and/or high yield sesame plants with shatter-resistant capsules are hybridized in that none of the disclosed varieties occurs in nature or in known worldwide sesame varieties. The high oil and/or high yield sesame plants with shatter-resistant capsules are characterized by the disclosed QTL markers which were judiciously detected in other varieties, selected and gradually introduced in the disclosed combinations to yield the disclosed high oil and/or high yield sesame plants with shatter-resistant capsules. Once specific disclosed high oil and/or high yield sesame plants with shatter-resistant capsules were achieved, further breeding was used to stabilize the varieties and assure constant phenotypes for sesame production, making the varieties pure lines. The term "hybridized" is used herein to define disclosed varieties having QTL markers and traits collected during the breeding process from different varieties that were determined and hybridized during the highly complicated computationally-supported breeding methods described below, in which the genotypes of multiple sesame varieties have been judiciously combined and analyzed, to discover and accumulate the recited QTL markers and corresponding phenotypical traits into the disclosed high oil and/or high yield sesame plant with shatter-resistant capsules. Although the recited sesame plants are not genetically modified by sequences originating from other species, they cannot be reached merely by natural processes, as is evident by the detailed and intentional breeding program that was applied to specifically measure required characteristics, detect corresponding markers using bioinformatics methods and combine the detected QTLs in the selected varieties by classic breeding approaches (e.g., hand pollination crosses and single plant selections). For example, any further generation derived from the disclosed high oil and/or high yield sesame plants with shatter-resistant capsules is also understood to be a high oil and/or high yield sesame plant with shatter-resistant capsules.

As described herein, six unique combinations of QTLs, referred to as QTL cassettes, were detected to differentiate disclosed breeding material (with shattering resistant capsules) from worldwide sesame lines. The cassettes' discovery was based on ca. 200 elite shatter resistant lines (disclosed, e.g., in U.S. Pat. No. 10,577,623) and a set of ca. 200 world accessions. Following the cassettes discovery, the disclosed germplasm was tested with respect to 656 world accessions to demonstrate their uniqueness, as being clearly distinct from known sesame varieties (see Table 5). The six cassettes share one common marker (QTL1) which is associated with the oil level I the sesame seeds. Moreover, other markers (QTLs 2-9) in the cassettes were found to be associated with various yield components.

Figure 1:
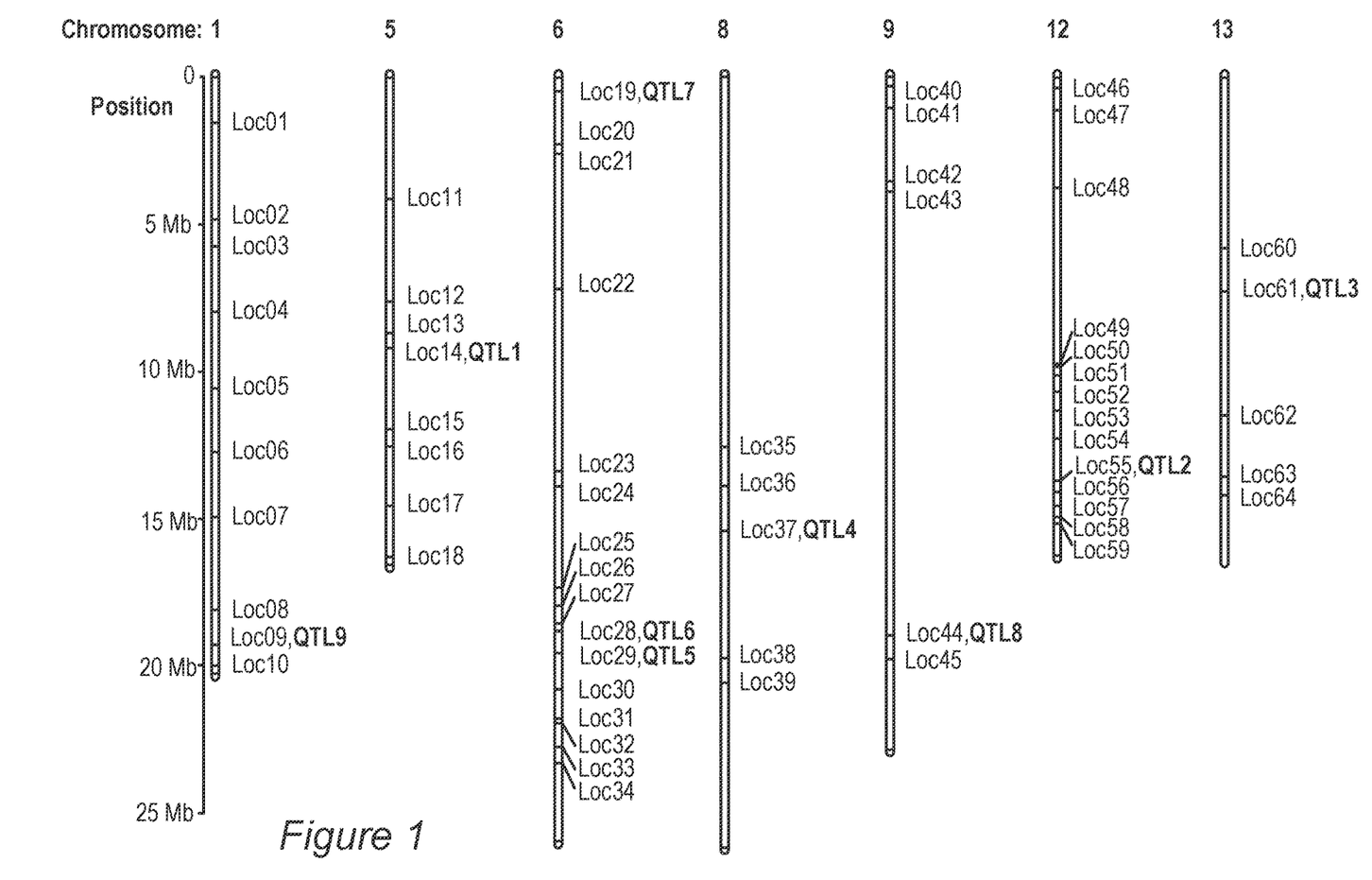
FIG. 1 is a high-level schematic illustration of sesame chromosomes with indications of the relevant markers' loci, according to some embodiments of the invention.

FIG. 1 is a high-level schematic illustration of sesame chromosomes with indications of the relevant markers' loci, according to some embodiments of the invention. FIG. 1 illustrates schematically seven of the thirteen sesame chromosomes and the marker locations indicated along them. Table 3 below lists all loci, their markers and their respective traits. The details of cassette composition are provided further below. The term "NIR Oil" denotes oil content measurements in the near infrared spectrum of ca. 500 sesame seeds (bulk) per line after harvesting using Perten Instruments DA 7200 NIR analysis system, calibrated for sesame seeds. The chromosomal position refers to the Genome V2.0 version (Wang et al. 2016, Updated sesame genome assembly and fine mapping of plant height and seed coat color QTLs using a new high-density genetic map. BMC Genomics 17:31).

Table 1 provides the derived genetic markers, QTLs, corresponding traits and resulting marker cassettes, according to some embodiments of the invention.

TABLE 1

Genetic markers, QTLs, corresponding traits and marker cassettes
with corresponding high oil and/or high yield components.

| QTL | SEQ ID NO | Chromosome-Position | QTL P-value | Phenotypic trait |
|---|---|---|---|---|
| 1 | 1, 2 | Chr5-9215531 | <0.05 | Oil level (NIR Oil) |
| 2 | 3, 4 | Chr12-13724834 | <0.05 | Oil level (NIR Oil) |
| 3 | 5, 6 | Chr13-7267144 | <0.05 | Yield (Number of capsules on lateral shoots |
| 4 | 7, 8 | Chr8-15457227 | <0.05 | Oil level (NIR Oil) |
| 5 | 9, 10 | Chr6-19580227 | <0.05 | Oil level (NIR Oil), Branching width |
| 6 | 11, 12 | Chr6-18811179 | <0.05 | Yield (Plant total height) |
| 7 | 13, 14 | Chr6-471385 | <0.05 | Oil level (NIR Oil) |
| 8 | 15, 16 | Chr9-18953887 | <0.05 | Yield (Plant total height, Seed average length) |
| 9 | 17, 18 | Chr1-19270856 | <0.05 | Yield (Number of capsules on the main stem) |

| QTL | SEQ ID NO | Allele 1 | Allele 2 | Cassette 1 | Cassette 2 | Cassette 3 | Cassette 4 | Cassette 5 | Cassette 6 |
|---|---|---|---|---|---|---|---|---|---|
| 1 | 1, 2 | A | G | AA | AA | AA | AA | AA | AA |
| 2 | 3, 4 | A | T | AA | TT/TA | TT/TA | TT/TA | | |
| 3 | 5, 6 | A | G | GG | GG | AA/AG | GG | GG | AA/AG |
| 4 | 7, 8 | A | G | | AA | AA/AG | AA | | AA/AG |
| 5 | 9, 10 | C | T | | TT/TC | TT/TC | CC | | |
| 6 | 11, 12 | A | G | | | AA/AG | | | AA/AG |
| 7 | 13, 14 | A | T | | | | AA/AT | | |
| 8 | 15, 16 | A | G | | | | | AA | AA |
| 9 | 17, 18 | C | T | | | | | CC/CT | CC/CT |

Disclosed high oil and/or high yield sesame plants with shatter-resistant capsules were derived by computationally supported breeding methods to yield plants which are different and distinct from any prior art sesame varieties. Specifically, disclosed high yield sesame plants have QTL 1 in common and are grouped herein by combinations of QTLs denoted in Table 1 as cassettes 1 through cassette 6.

Tables 2 and 3 present all analyzed genetic markers (including QTLs 1-9) with their respective traits, QTLs, according to some embodiments of the invention. The traits are numbered 1-20 and are related to loci numbered 1-64 of the sesame genome, as illustrated schematically in FIG. 1.

TABLE 2

Phenotypic traits that relate to high oil and/or high yield components and their respective markers' loci.

| Trait | Description | Marker loci associated with the trait (see Table 3) |
|---|---|---|
| Tr01 | Fruit length | Loc24, Loc52, Loc53 |
| Tr02 | Fruit seed number per capsule | Loc07, Loc41 |
| Tr03 | Carbohydrates | Loc03, Loc10, Loc30, Loc31, Loc32, Loc33 |
| Tr04 | NIR Oil | Loc02, Loc14, Loc19, Loc20, Loc21, Loc29, Loc37, Loc55 |
| Tr05 | NIR free fatty acids value | Loc26 |
| Tr06 | NIR oleic acid value | Loc16, Loc17, Loc18, Loc31, Loc39, Loc51, Loc54, Loc56 |
| Tr07 | Branching value | Loc04 |
| Tr08 | Branching width (the maximal width between two opposite lateral shoots) | Loc29 |
| Tr09 | Plant height to first capsule | Loc06, Loc32, Loc34, Loc58 |
| Tr10 | Plant total height | Loc08, Loc12, Loc25, Loc28, Loc44, Loc50, Loc59 |
| Tr11 | Seed average area | Loc01, Loc35, Loc45 |
| Tr12 | Seed average length | Loc05, Loc11, Loc40, Loc41, Loc43, Loc44, Loc45, Loc63 |
| Tr13 | Seed average width | Loc01, Loc13, Loc16, Loc22, Loc36, Loc57, Loc63 |
| Tr14 | Seed color defined by the L shade (in the "Lab" standard method) | Loc15, Loc23, Loc38, Loc41, Loc42, Loc46, Loc47, Loc49, Loc50, Loc60, Loc62 |
| Tr15 | Seed size uniformity | Loc17, Loc48 |
| Tr16 | Thousand grain weight | Loc15 |

TABLE 2-continued

Phenotypic traits that relate to high oil and/or high yield components and their respective markers' loci.

| Trait | Description | Marker loci associated with the trait (see Table 3) |
|---|---|---|
| Tr18 | Capsules number lateral shoots | Loc61 |
| Tr19 | Capsules number main stem | Loc09, Loc64 |
| Tr20 | Total number of capsules | Loc27, Loc59 |

It is noted that some of the traits directly relate to the oil content and/or composition of the sesame seeds, such as traits 4 and 6, while other traits relate to yield traits which can also be used to increase the overall oil quantity in the harvested seeds, by increasing the amount of seeds. Together, increased oil content and/or increased yield contribute to an overall increase in the amount of harvested oil from the sesame crop. For example, certain disclosed varieties increase the oil content by at least 1% and/or increase the yield by at least 15% (as average values) with respect to sesame varieties that do not include the disclosed cassettes. In various embodiments, certain disclosed varieties increase the oil content by any of at least 1%, at least 2%, at least 3% or at least 4% with respect to sesame varieties that do not include the disclosed cassettes. In some embodiments, certain disclosed varieties increase the yield by any of at least 15%, at least 20%, at least 30% or at least 35% with respect to sesame varieties that do not include the disclosed cassettes. In various embodiments, certain disclosed varieties combine increases in oil content with increased yield. Table 4 provides non-limiting examples for the improved performance of some of the disclosed varieties.

TABLE 3

Analyzed genetic markers (including QTLs 1-9), their loci and their respective traits.

| Marker loci and QTLs | Chromosome-Position | Traits |
|---|---|---|
| Loc01 | 1-1565868 | Tr11, Tr13 |
| Loc02 | 1-4825566 | Tr04 |
| Loc03 | 1-5736565 | Tr03 |
| Loc04 | 1-7948510 | Tr07 |
| Loc05 | 1-10573817 | Tr12 |
| Loc06 | 1-12741107 | Tr09 |
| Loc07 | 1-14941186 | Tr02 |
| Loc08 | 1-18095873 | Tr10 |
| Loc09, QTL9 | 1-19270856 | Tr19, |
| Loc10 | 1-20018096 | Tr03 |
| Loc11 | 5-4144840 | Tr12 |
| Loc12 | 5-7625388 | Tr10 |
| Loc13 | 5-8676190 | Tr13 |
| Loc14, QTL1 | 5-9215531 | Tr04 |
| Loc15 | 5-11962028 | Tr16, Tr14 |
| Loc16 | 5-12538680 | Tr06, Tr13 |
| Loc17 | 5-14594735 | Tr15, Tr06 |
| Loc18 | 5-16297886 | Tr06 |
| Loc19, QTL7 | 6-471385 | Tr04 |
| Loc20 | 6-2290397 | Tr04 |
| Loc21 | 6-2595046 | Tr04 |
| Loc22 | 6-7212057 | Tr13 |
| Loc23 | 6-13398596 | Tr14 |
| Loc24 | 6-13907692 | Tr01 |
| Loc25 | 6-17339135 | Tr10 |
| Loc26 | 6-17949954 | Tr05 |
| Loc27 | 6-18569882 | Tr20 |
| Loc28, QTL6 | 6-18811179 | Tr10, |
| Loc29, QTL5 | 6-19580227 | Tr04, Tr08 |
| Loc30 | 6-20794763 | Tr03 |
| Loc31 | 6-21794639 | Tr03, Tr06 |

TABLE 3-continued

Analyzed genetic markers (including QTLs 1-9), their loci and their respective traits.

| Marker loci and QTLs | Chromosome-Position | Traits |
|---|---|---|
| Loc32 | 6-21918155 | Tr09, Tr03 |
| Loc33 | 6-22739924 | Tr03 |
| Loc34 | 6-23288849 | Tr09 |
| Loc35 | 8-12548680 | Tr11 |
| Loc36 | 8-13882426 | Tr13 |
| Loc37, QTL4 | 8-15457227 | Tr04 |
| Loc38 | 8-19757189 | Tr14 |
| Loc39 | 8-20598731 | Tr06 |
| Loc40 | 9-322521 | Tr12 |
| Loc41 | 9-1044302 | Tr12, Tr14, Tr02 |
| Loc42 | 9-3517779 | Tr14 |
| Loc43 | 9-3933482 | Tr12 |
| Loc44, QTL8 | 9-18953887 | Tr10, Tr12 |
| Loc45 | 9-19793931 | Tr11, Tr12 |
| Loc46 | 12-393990 | Tr14 |
| Loc47 | 12-1117586 | Tr14 |
| Loc48 | 12-3784791 | Tr15 |
| Loc49 | 12-9756633 | Tr14 |
| Loc50 | 12-9839791 | Tr10, Tr14 |
| Loc51 | 12-10126949 | Tr06 |
| Loc52 | 12-10726250 | Tr01 |
| Loc53 | 12-11333887 | Tr01 |
| Loc54 | 12-12293861 | Tr06 |
| Loc55, QTL2 | 12-13724834 | Tr04 |
| Loc56 | 12-14083288 | Tr06 |
| Loc57 | 12-14593306 | Tr13 |
| Loc58 | 12-14944091 | Tr09 |
| Loc59 | 12-15161646 | Tr20, Tr10 |
| Loc60 | 13-5809997 | Tr14 |
| Loc61, QTL3 | 13-7267144 | Tr18 |
| Loc62 | 13-11499912 | Tr14 |
| Loc63 | 13-13555490 | Tr12, Tr13 |
| Loc64 | 13-14203342 | Tr19 |

Table 4 provides the effects of sesame varieties with different cassette combinations on the oil content and/or on the yield of the respective varieties, compared to lines not expressing any of the cassettes.

TABLE 4

Oil content and yield enhancement of sesame varieties with different cassette combinations, compared to lines not expressing any of the cassettes.

| Cassette | | | | | | Effect on | |
|---|---|---|---|---|---|---|---|
| 1 | 2 | 3 | 4 | 5 | 6 | Oil content | Yield |
| Included | | | Included | Included | | Yes: 5.48% | No |
| Included | | | Included | | | No | Yes: 36.94% |
| Included | | | | | | Yes: 1.33% | No |
| | Included | | Included | | | Yes: 4.64% | No |

TABLE 4-continued

Oil content and yield enhancement of sesame varieties with different cassette combinations, compared to lines not expressing any of the cassettes.

| Cassette | | | | | | Effect on | |
|---|---|---|---|---|---|---|---|
| 1 | 2 | 3 | 4 | 5 | 6 | Oil content | Yield |
| Included | | | | | | Yes: 4.01% | Yes: 15.65% |
| | Included | | Included | | | No | Yes: 35.98% |
| | | Included | | | | Yes: 1.67% | Yes: 17.97% |
| | | | | Included | | Yes: 2.37% | Yes: 36.82% |
| | | | | | Included | Yes: 3.1% | Yes: 37.91% |

A total of 2643 varieties are thus shown to be included in one of the combinations of disclosed cassettes, while none of the world varieties that were examined includes any of the cassette combinations. All disclosed varieties are shatter resistant and characterized by high oil content and/or by high yield.

Advantageously, disclosed embodiments provide sesame plants with high oil and/or high yield that may improve the nutritional value of the sesame seeds, may increase oil produced from the sesame seeds and may make sesame growing profitable even in developed countries. As used herein, a "high oil" content sesame plant means a sesame plant having an improvement of at least a 1% increase in oil content compared to sesame variety ES107 not expressing any of the marker cassettes described herein and as used herein a "high yield" sesame plant means a sesame plant having at least a 15% increase in yield compared to sesame variety ES107; such "high oil" content and/or "high yield" sesame plants are provided according to some embodiments of the invention.

QTL 1, as used herein, refers to a polymorphic genetic locus linked to a genetic marker at position 9215531 on sesame chromosome 5. The two alleles of the genetic marker at QTL 1 have the SNP bases "A" or "G", as set forth respectively in the nucleic acid sequences of SEQ ID NOs 1 and 2. In all six cassettes 1-6. QTL 1 is homozygous for allele 1 (SEQ ID NO 1).

SEQ ID NO 1 (SNP base bold):
TTTACCTAATGAGGTACAAGTCTGAGGCCTTTGGAAGGTTCAAGGAGTACA

GACTTGAAGTCAAGAATCAAACTAGCCGTAAATTAAAACCCTTCGATCAAA

CTGAGGCAGAGAGTATTTAAGTGGTGAATTTGTTGATTACTTAAAAGAGAA

TGGAATTCTCACTCAATGGACTCCTCTTGAACGCCATAACTTAATAGC

SEQ ID NO 2 (SNP base bold):
TTTACCTAATGAGGTACAAGTCTGAGGCCTTTGGAAGGTTCAAGGAGTACA

GACTTGAAGTCAAGAATCAAACTAGCCGTAAATTAAAACCCTTCGATCAGA

CTGAGGCAGAGAGTATTTAAGTGGTGAATTTGTTGATTACTTAAAAGAGAA

TGGAATTCTCACTCAATGGACTCCTCTTGAACGCCATAACTTAATAGC

QTL 2, as used herein, refers to a polymorphic genetic locus linked to a genetic marker at position 13724834 on sesame chromosome 12. The two alleles of the genetic marker at QTL 2 have the SNP bases "A" or "T", as set forth respectively in the nucleic acid sequences of SEQ ID NOs 3 and 4. In cassette 1. QTL 2 is homozygous for allele 1 (SEQ ID NO 3), while in cassettes 2, 3 and 4, QTL 2 may be homozygous for allele 2 (SEQ ID NO 4) or be heterozygous (SEQ ID NOs 3 and 4).

SEQ ID NO 3 (SNP base bold):
CTAAGTCAGTTCTTTTCATTATACACGGAATGGGCACTGGAGTTTTGAAGG

AGCGTGTGCTTGAACTACTAAGAAACCATCCACGCATTGCAAAGTTTGAAC

AGGAAAGCCCAATGAATTATGGTTGTACAGTAGCCTATATCAAGTGAACGT

GTGATTGTATCAGCTATCAAGAAGGCAGTGATATTCTTTGAATTTTGT

SEQ ID NO 4 (SNP base bold):
CTAAGTCAGTTCTTTTCATTATACACGGAATGGGCACTGGAGTTTTGAAGG

AGCGTGTGCTTGAACTACTAAGAAACCATCCACGCATTGCAAAGTTTGATC

AGGAAAGCCCAATGAATTATGGTTGTACAGTAGCCTATATCAAGTGAACGT

GTGATTGTATCAGCTATCAAGAAGGCAGTGATATTCTTTGAATTTTGT

QTL 3, as used herein, refers to a polymorphic genetic locus linked to a genetic marker at position 7267144 on sesame chromosome 13. The two alleles of the genetic marker at QTL 3 have the SNP bases "A" or "G", as set forth respectively in the nucleic acid sequences of SEQ ID NOs 5 and 6. In cassettes 1, 2, 4 and 5. QTL 3 is homozygous for allele 2 (SEQ ID NO 6), while in cassettes 3 and 6. QTL 3 may be homozygous for allele 1 (SEQ ID NO 5) or be heterozygous (SEQ ID NOs 5 and 6).

SEQ ID NO 5 (SNP base bold):
CGTTAACAGAGAGTGTATGAGGATGCTGTCTCGGAGGGAAATCCCAAGAAA

TATAGTGCATGTCATGGTTGACAACGGTTGGGACAAACTCTGGAGCATTAC

AGATAACAGTCTGGAAATAGCCTTCTGGGGAGGAAACGAAGTTTGAGTAGT

ACATGAGAAGGGTTCTTGGGAGATTATCCCAACCCCATATGCAGTACT

SEQ ID NO 6 (SNP base bold):
CGTTAACAGAGAGTGTATGAGGATGCTGTCTCGGAGGGAAATCCCAAGAAA

TATAGTGCATGTCATGGTTGACAACGGTTGGGACAAACTCTGGAGCATTGC

AGATAACAGTCTGGAAATAGCCTTCTGGGGAGGAAACGAAGTTTGAGTAGT

ACATGAGAAGGGTTCTTGGGAGATTATCCCAACCCCATATGCAGTACT

QTL 4, as used herein, refers to a polymorphic genetic locus linked to a genetic marker at position 15457227 on sesame chromosome 8. The two alleles of the genetic marker at QTL 4 have the SNP bases "A" or "G", as set forth respectively in the nucleic acid sequences of SEQ ID NOs 7 and 8. In cassettes 2 and 4, QTL 4 is homozygous for allele 1 (SEQ ID NO 7), while in cassettes 3 and 6, QTL 4 may be homozygous for allele 1 (SEQ ID NO 7) or be heterozygous (SEQ ID NOs 7 and 8).

SEQ ID NO 7 (SNP base bold):
GCACTGCAACGCTGGACTCAAGTTTCAACACCTCAACACCCCCATACTCAG

TGTAAGTCCAGGCCITCATCTCTGATGGAATGGAAGAAGAACTCTTGTTAG

AGGCGGTCTCAGCAGAAGGAGGAGAAGTTGCAAATACTCTGAGAGGTTGAG

GGCCAAA

SEQ ID NO 8 (SNP base bold):
GCACTGCAACGCTGGACTCAAGTTTCAACACCTCAACACCCCCATACTCAG

TGTAAGTCCAGGCCTTCATCTCTGATGGGATGGAAGAAGAACTCTTGTTAG

```
AGGCGGTCTCAGCAGAAGGAGCAGAAGTTGCAAATACTCTGAGAGGTTGAG

GGCCAAA
```

QTL 5, as used herein, refers to a polymorphic genetic locus linked to a genetic marker at position 19580227 on sesame chromosome 6. The two alleles of the genetic marker at QTL 5 have the SNP bases "C" or "T", as set forth respectively in the nucleic acid sequences of SEQ ID NOs 9 and 10. In cassettes 2 and 3, QTL 5 may be homozygous for allele 2 (SEQ ID NO 10) or be heterozygous (SEQ ID NOs 9 and 10), while in cassette 4, QTL 5 is homozygous for allele 1 (SEQ ID NO 9).

```
SEQ ID NO 9 (SNP base bold):
TATACTTGCCATATGATTGATTCAAATTTGATCGAGTCGAGTCTGAATTAT

AATTTTTCATATTTTTAAGGGATGATTCGGCTAGATAAGACAATTTTTCCA

AACCAAATGAAATTCACCGCTTAACTATTTTCATCTTTGATCAAATTAAAG

AGTTTCCACTACTTCGTTGATCTAATTTTGGGTTAAATACAGTTTACT

SEQ ID NO 10 (SNP base bold):
TATACTTCCATATGATTGATTCAAATTTGATCGAGTCGAGTCTGAATTATA

ATTTTTCATATTTTTAAGGGATGATTCGGCTAGATAAGACAATTTTTCTAA

ACCAAATGAAATTCACCGCTTAACTATTTTCATCTTTGATCAAATTAAAGA

GTTTCCACTACTTGCTTGATCTAATTTTGGGTTAAATACAGTTTACT
```

QTL 6, as used herein, refers to a polymorphic genetic locus linked to a genetic marker at position 18811179 on sesame chromosome 6. The two alleles of the genetic marker at QTL 6 have the SNP bases "A" or "G", as set forth respectively in the nucleic acid sequences of SEQ ID NOs 11 and 12. In cassettes 3 and 6, QTL 6 may be homozygous for allele 1 (SEQ ID NO 11) or be heterozygous (SEQ ID NOs 11 and 12).

```
SEQ ID NO 11 (SNP base bold):
GGGCTCATCTGATCATGTACACACAAATACTATGTACCACTGCGGAACATT

TTTTGTCCTATGACTTAGGGCCTTTTTACTTTTGGTTCCATTGGTTATGAA

ATTTTCAATTTTGGTCCAATAACTTTAAAAAAATAGCACTTTTGGCCCGTG

ACATATTTTCATTAGATATTTAAAGCAAAAGACCACGTGTGGCCGTTA

SEQ ID NO 12 (SNP base bold):
GGGCTCATCTGATCATGTACACACAAATACTATGTACCACTGCGGAACATT

TTTTGTCCTATGACTTAGGGCCTTTTTACTTTTGGTTCCATTGGTTATGGA

ATTTTCAATTTTGGTCCAATAACTTTAAAAAAATAGCACTTTTGGCCCGTG

ACATATTTTCATTAGATATTTAAAGCAAAAGACCACGTGTGGCCGTTA
```

QTL 7, as used herein, refers to a polymorphic genetic locus linked to a genetic marker at position 471385 on sesame chromosome 6. The two alleles of the genetic marker at QTL 7 have the SNP bases "A" or "T", as set forth respectively in the nucleic acid sequences of SEQ ID NOs 13 and 14. In cassette 4, QTL 7 may be homozygous for allele 1 (SEQ ID NO 13) or be heterozygous (SEQ ID NOs 13 and 14).

```
SEQ ID NO 13 (SNP base bold):
CTGTTTGATTAGAAAGCTGGATCATGTTGTGCAAATAACAATTTTCTATTC

CAGAATACTACTGCAGGCTGTGGGACTCGCTGATTTTGGCTCAAGAAATAG

TCAATAATCATTTACTTGAAGCATAATTACTCCAAGAATTTTAGGATTGTA

TATTTCGTGAATTCGAACAAGAATTGCCCGTGACCAGTTGCCATCTGA

SEQ ID NO 14 (SNP base bold):
CTGTTTGATTAGAAAGCTGGATCATGTTGTGCAAATAACAATTTTCTATTC

CAGAATACTACTGCAGGCTGTGGGACTCGCTGATTTTGGCTCAAGAAATTG

TGAATAATCATTTACTTGAAGCATAATTACTCCAAGAATTTTAGGATTGTA

TATTTCGTGAATTCGAACAAGAATTGCCCGTGACCAGTTGCCATCTGA
```

QTL 8, as used herein, refers to a polymorphic genetic locus linked to a genetic marker at position 18953887 on sesame chromosome 9. The two alleles of the genetic marker at QTL 8 have the SNP bases "A" or "G", as set forth respectively in the nucleic acid sequences of SEQ ID NOs 15 and 16. In cassettes 5 and 6, QTL 8 is homozygous for allele 1 (SEQ ID NO 15).

```
SEQ ID NO 15 (SNP base bold):
ATCATGAATTTTACTCCTATTTTTTTGTTAATATTAACAAATCTAGTGGAT

TTTGACTAACAAAGGGACTTATTTTATTAAACGAAAGCAACCTTCAAGGAT

ATTAAATATAATTTTTCAAACCACATGAGATTTATATGCAATTACATTAAA

TTTCGGTAGAGTGGAGTAGTTATCCCTAGAAATATTACAGTCGAAGTG

SEQ ID NO 16 (SNP base bold):
ATCATGAATTTTACTCCTATTTTTTTGTTAATATTAACAAATCTAGTGGAT

TTTGACTAACAAAGGGACTTATTTTATTAAACGAAAGCAACCTTCAAGGGT

ATTAAATATAATTTTTCAAACCACATGAGATTTATATGCAATTACATTAAA

TTTCGGTAGAGTGGAGTAGTTATCCCTAGAAATATTACAGTCGAAGTG
```

QTL 9, as used herein, refers to a polymorphic genetic locus linked to a genetic marker at position 19270856 on sesame chromosome 1. The two alleles of the genetic marker at QTL 9 have the SNP bases "C" or "T", as set forth respectively in the nucleic acid sequences of SEQ ID NOs 17 and 18. In cassettes 5 and 6, QTL 9 may be homozygous for allele 1 (SEQ ID NO 17) or be heterozygous (SEQ ID NOs 17 and 18).

```
SEQ ID NO 17 (SNP base bold):
TATTTATTACTTGTATTTCTTCTTGATTAGCTCGCAAGATTGGAAGGGACG

ACTAAAATTACCACCAGGAGACACTCGTTATAGAACCGAGGTAAGTTTCCT

GTAATATGCCAGTTTGTGAACTGGTTGTTGAAACAAACATCTTTATTATTA

TTTTTATTTGCCTTTCAGGATGTTACAGCTACCAAAGGAAATGAATTT

SEQ ID NO 18 (SNP base bold):
TATTTATTACTTGTATTTCTTCTTGATTAGCTCGCAAGATTGGAAGGGACG

ACTAAAATTACCACCAGGAGACACTCGTTATAGAACCGAGGTAAGTTTCTT

GTAATATGCCAGTTTGTGAACTGGTTGTTGAAACAAACATCTTTATTATTA

TTTTTATITGCCTTTCAGGATGTTACAGCTACCAAAGGAAATGAATTT
```

High oil and/or high yield sesame plants with shatter-resistant capsules, progeny thereof and/or part(s) thereof are provided, the sesame plants comprising a plurality of quantitative trait loci (QTLs) having a corresponding plurality of nucleic acid genetic markers that are associated with a plurality of phenotypic traits of the sesame plant comprising at least an oil level trait and a yield trait, wherein the QTLs are combined in the sesame plant from a plurality of sesame varieties by computationally supported breeding. The QTLs comprise QTL 1 associated with high oil content, with corresponding markers set forth in SEQ ID NOs 1 or 2, wherein the sesame plant or part thereof is homozygous with respect to SEQ ID NO 1. The sesame plants further comprise at least one of: QTLs 2, 3 and/or QTLs 2, 3, 4, 5 and/or QTLs 2, 3, 4, 5, 7 and/or QTLs 3, 8, 9 and/or QTLs 3, 4, 6, 8, 9. These combinations include all disclosed cassettes 1-6, as shown below.

In certain embodiments, referred to herein as cassette 1, the QTLs further comprise QTL 2 associated with high oil content, with corresponding markers set forth in SEQ ID NOs 3 or 4, and wherein the sesame plant or part thereof is homozygous with respect to SEQ ID NO 3, and QTL 3 associated with high yield (e.g., the number of capsules on lateral shoots), with corresponding markers set forth in SEQ ID NOs 5 or 6, and wherein the sesame plant or part thereof is homozygous with respect to SEQ ID NO 6.

In certain embodiments, the QTLs further comprise QTL 2 associated with high oil content, with corresponding markers set forth in SEQ ID NOs 3 or 4, and wherein the sesame plant or part thereof is homozygous with respect to SEQ ID NO 4 or heterozygous, QTL 3 associated with high yield (e.g., the number of capsules on lateral shoots), with corresponding markers set forth in SEQ ID NOs 5 or 6, and wherein the sesame plant or part thereof is homozygous with respect to SEQ ID NO 6, and QTL 4 associated with high oil content, with corresponding markers set forth in SEQ ID NOs 7 or 8, and wherein the sesame plant or part thereof is homozygous with respect to SEQ ID NO 7. For example, referred to herein as cassette 2, the QTLs may further comprise QTL 5 associated with high oil content and high yield (e.g., the branching width), with corresponding markers set forth in SEQ ID NOs 9 or 10, and wherein the sesame plant or part thereof is homozygous with respect to SEQ ID NO 10 or heterozygous. In another example, referred to herein as cassette 4, the QTLs may further comprise QTL 5 associated with high oil content and high yield (e.g., the branching width), with corresponding markers set forth in SEQ ID NOs 9 or 10, and wherein the sesame plant or part thereof is homozygous with respect to SEQ ID NO 9, and QTL 7 associated with high oil content, with corresponding markers set forth in SEQ ID NOs 13 or 14, and wherein the sesame plant or part thereof is homozygous with respect to SEQ ID NO 13 or heterozygous.

In certain embodiments, referred to herein as cassette 3, the QTLs further comprise QTL 2 associated with high oil content, with corresponding markers set forth in SEQ ID NOs 3 or 4, and wherein the sesame plant or part thereof is homozygous with respect to SEQ ID NO 4 or heterozygous, QTL 3 associated with high yield (e.g., the number of capsules on lateral shoots), with corresponding markers set forth in SEQ ID NOs 5 or 6, and wherein the sesame plant or part thereof is homozygous with respect to SEQ ID NO 6 or heterozygous. QTL 4 associated with high oil content, with corresponding markers set forth in SEQ ID NOs 7 or 8, and wherein the sesame plant or part thereof is homozygous with respect to SEQ ID NO 7 or heterozygous. QTL 5 associated with high oil content and high yield (e.g., the branching width), with corresponding markers set forth in SEQ ID NOs 9 or 10, and wherein the sesame plant or part thereof is homozygous with respect to SEQ ID NO 10 or heterozygous, and QTL 6 associated with high yield (e.g., the plant total height), with corresponding markers set forth in SEQ ID NOs 11 or 12, and wherein the sesame plant or part thereof is homozygous with respect to SEQ ID NO 11 or heterozygous.

In certain embodiments, the QTLs further comprise QTL 8 associated with high yield (e.g., the plant total height and the average length of the seeds), with corresponding markers set forth in SEQ ID NOs 15 or 16, and wherein the sesame plant or part thereof is homozygous with respect to SEQ ID NO 15, and QTL 9 associated with high yield (e.g., the number of capsules on the main stem), with corresponding markers set forth in SEQ ID NOs 17 or 18, and wherein the sesame plant or part thereof is homozygous with respect to SEQ ID NO 17 or heterozygous. For example, referred to herein as cassette 5, the QTLs may further comprise QTL 3 associated with high yield (e.g., the number of capsules on lateral shoots), with corresponding markers set forth in SEQ ID NOs 5 or 6, and wherein the sesame plant or part thereof is homozygous with respect to SEQ ID NO 6. In another example, referred to herein as cassette 6, the QTLs may further comprise QTL 3 associated with high yield (e.g., the number of capsules on lateral shoots), with corresponding markers set forth in SEQ ID NOs 5 or 6, and wherein the sesame plant or part thereof is homozygous with respect to SEQ ID NO 5 or heterozygous, QTL 4 associated with high oil level, with corresponding markers set forth in SEQ ID NOs 7 or 8, and wherein the sesame plant or part thereof is homozygous with respect to SEQ ID NO 7 or heterozygous, and QTL 6 associated with high yield (e.g., the plant total height), with corresponding markers set forth in SEQ ID NOs 11 or 12, and wherein the sesame plant or part thereof is homozygous with respect to SEQ ID NO 11 or heterozygous.

Table 5 illustrates the uniqueness of the disclosed varieties, as characterized by cassettes 1-6 and their combinations, according to some embodiments of the invention, with respect to the world varieties. The number of disclosed varieties is indicated with respect to the combination of marker cassettes which characterize the respective varieties.

TABLE 5

Comparison of disclosed varieties included in the disclosed cassettes with world (prior art) varieties.

| Cassette combination | | | | | | Number of varieties | |
|---|---|---|---|---|---|---|---|
| | | | | | | Disclosed (of total - 5310) | World (of total - 656) |
| 1 | 2 | 3 | 4 | 5 | 6 | | |
| | | | | | Included | 22 | 0 |
| | | | | Included | | 126 | 0 |
| | | | Included | | | 15 | 0 |
| | | | Included | Included | | 42 | 0 |
| | | Included | | | | 283 | 0 |
| | | Included | | | Included | 346 | 0 |
| | Included | | | | | 692 | 0 |
| | Included | | | Included | | 329 | 0 |
| Included | | | | | | 474 | 0 |
| Included | | | | Included | | 312 | 0 |
| Included | | | | Included | Included | 2 | 0 |

Figure 2:
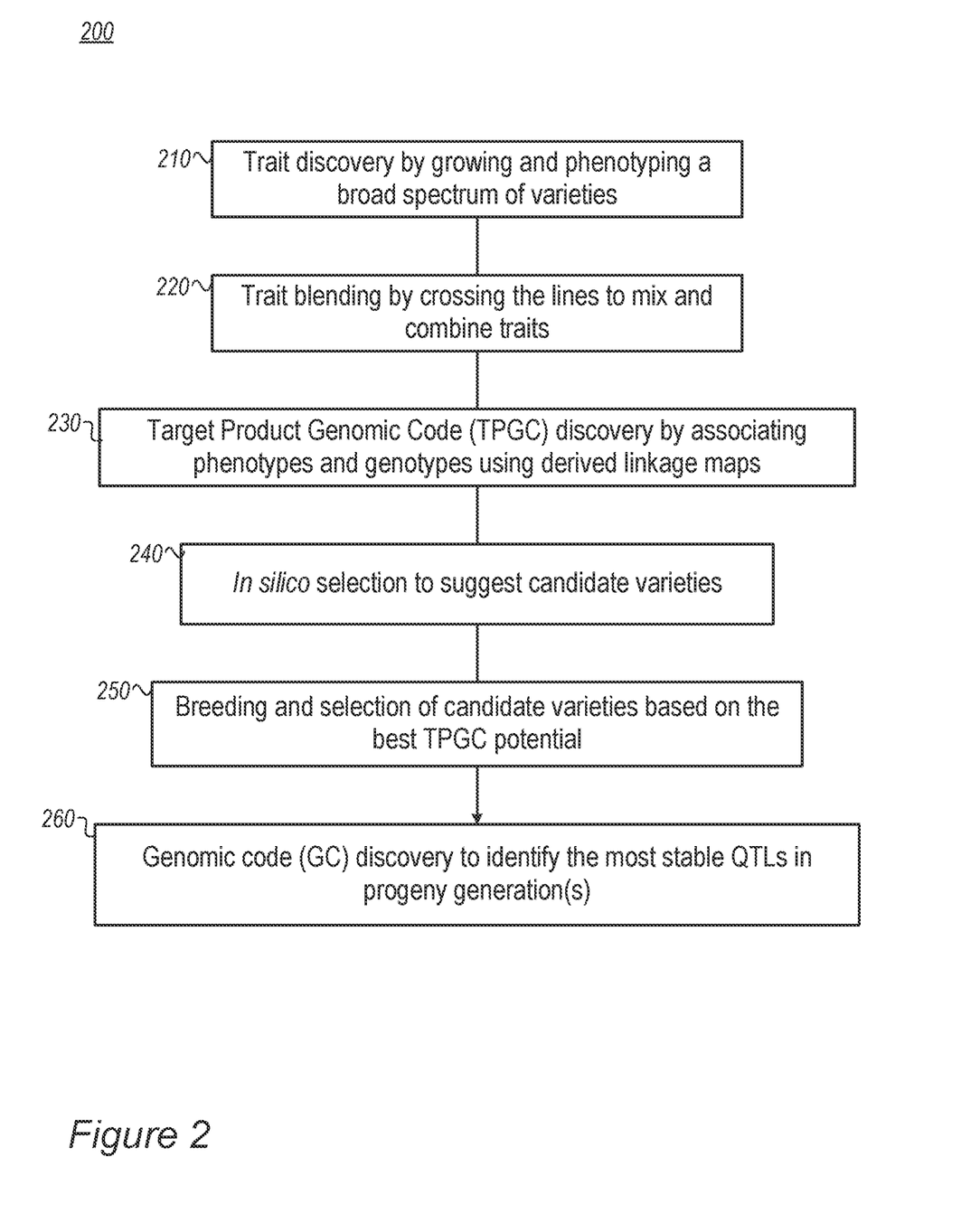
FIG. 2 is a high-level schematic illustration of a computationally supported breeding method, according to some embodiments of the invention.

FIG. 2 is a high-level schematic illustration of a computationally supported breeding method 200, according to some embodiments of the invention. Method 200 may be at least partially implemented by at least one computer processor; computationally supported breeding method 200 is used to detect and combine QTLs from a plurality of sesame varieties to develop disclosed high yield sesame plants with shatter-resistant capsules which are different than any of the parent varieties by virtue of the achieved phenotypical and/or yield characteristics.

Computationally supported breeding method 200 comprises stages of trait discovery by growing and phenotyping a broad spectrum of varieties (stage 210), trait blending by developing hybridized lines through crossing the selected lines to mix and combine traits and selfing of the progeny in subsequent generations (stage 220), Target Product Genomic Code (TPGC) discovery by associating phenotypes and genotypes using derived linkage maps (stage 230), in silico selection to suggest candidate varieties (stage 240), breeding candidate varieties and selection of varieties based on the best TPGC potential (stage 250) and genomic code (GC) discovery to identify the most stable QTLs in hybridized progeny generation(s) (stage 260), as explained in detail below. TPGC discovery 230, in silico validation 250 and GC discovery 260 are based on computational algorithms that cannot be performed manually and provide the computational support for the judicious selection of the varieties that are generated and further crossed during the development process to yield disclosed high oil and/or high yield sesame plants with shatter-resistant capsules. It is noted that during the discovery phase, the QTLs are derived in order to combine them (by hybridization) to create unique combinations of QTLs which do not exist in known world lines.

In certain embodiments, sesame lines were bred to reach high oil and/or high yield levels by collecting various sesame lines worldwide, creating F2 linkage populations, applying intensive phenotyping and genotyping of thousands of sesame lines, predicting of QTLs affecting the oil and/or yield level trait, and establishing unique marker combinations, termed "marker cassettes" herein, to characterize novel high oil and/or high yield lines provided by the methods described herein and not existing in commercial or natural lines.

The breeding methodology was based on algorithms for deriving the Target Product Genomic Code (TPGC) to associate (i) the Target Product (TP) being defined in advance based on market requirements and including a set of desired attributes (traits) that are available in natural genetic variations; and (ii) the Genomic Code (GC) comprising set(s) of genomic regions that include quantitative trait loci (QTLs) that affect and are linked to the TP traits. The algorithms may be configured to calculate multiple genomic interactions and to maximize the genomic potential of specific plants for the development of new varieties. The breeding program was constructed to derive the TPGC, and then by crossing and selfing to achieve a product which contains the specific GC that corresponds to the required TPs.

Certain embodiments of the breeding process of developing lines, through crossing and successive generations of selfing comprise stages such as: (i) Trait Discovery, in which a broad spectrum of varieties from different geographies and worldwide sources are grown and phenotyped in order to discover new traits that can potentially be combined to create new varieties; (ii) Trait Blend, in which a crossing cycle is carried out based on phenotypic assumption(s), in which the different traits are mixed and combined. Initial trait cycle(s) are followed by additional cycle(s) to create F2 (and possibly higher generations) population(s) that provide the basis for algorithmic analysis for constructing the TPGC; (iii) TPGC Discovery, in which the plant(s) are phenotyped and genotyped to produce linkage map(s), discovering the relevant QTLs and deriving the TPGC; (iv) several line validation stages over several years in which sesame lines based on millions of in silico calculated variations (and/or selections) are grown and are used to define the initial varieties; (v) Trait TPGC Blend, in which accurate crossings are performed in order to calculate the most efficient way to reach the best TPGC. The crossings are performed after in silico selection from millions of combinations, and are based, at least in part on phenotype assumptions; and (vi) Consecutive algorithm-based GC discovery stage(s) applied to F2 (or higher generation) population(s) grown in additional cycle(s).

Defining the TP for high oil and/or high yield shatter-resistant sesame varieties includes the development of high throughput methods for high oil and/or high yield level identification.

In the following non-limiting example of the process, Trait Discovery (i) was based on proprietary germplasm including hundreds of elite varieties and thousands of F2 individual plants and also 219 different sesame lines that were obtained from the U.S. National Plant Germplasm System (NPGC) and courtesy of professor Amram Ashri's sesame germplasm collection (see Ashri. A. 1998, Sesame Breeding. In: Janick J. (ed.). Plant Breeding Reviews Vol. 16. John Wiley and Sons, Somerset, N.J., pp. 179-228). These lines were used for the Trait Blend stage (ii), with crosses executed based on the potential for enrichment of genomic diversity to create new complex(es) of traits for the high oil and/or high yield level as the initial step for the TP-directed breeding program for high oil and/or high yield sesame lines. The resulting F1 hybrids were later self-crossed to create F2 linkage populations that showed phenotypic segregation. The F2 populations were then planted in three different environments for discovering the TPGC (iii) that includes high oil and/or high yield traits. After screening and deep phenotyping of 2500 individuals, a set of ca. 300 representatives was selected. The selected individuals from the F2 populations were further massively phenotyped for traits associated with oil and/or yield, as detailed in the following description. The measurement results were summarized into the representative high oil and/or high yield level traits.

TPGC Discovery (iii) included genotyping ca. 2500 selected individual plants from six populations. The analysis was performed with a panel of 1000 markers based on single nucleotide polymorphism (SNP) and directly designed based on the polymorphism found in the parental lines of the populations which were analyzed in depth using high throughput DNA sequencing technologies. The panel was designed to maximize the chance to have the largest number of common segregating SNPs in order to create highly similar linkage maps for all observed populations. The computation of linkage maps was executed on each linkage F2 population based on the genotyping results. Linkage maps were computed with MultiPoint, an interactive package for ordering multilocus genetic maps, and verification of maps was based on resampling techniques. Discovery of QTLs that are related to high oil and/or high yield level was carried out with the MultiQTL package, based on the linkage maps that were merged by Multipoint and the F2 population phenotype data, and using multiple interval mapping (MIM). The significance and co-occurrences of the high protein level and protein content markers were evaluated using an algorithm that related the genotype-phase of each marker to respective QTLs and traits in linkage maps of the six F2 populations (also called "linkage F2 populations" herein) in each population, for populations in different environments. QTL significance was computed with permutation, bootstrap tools and FDR (false discovery rate) for total analysis. The linkage maps of all six F2 populations and the information of the high oil and/or high yield level traits over all genotyped plants belonging to those populations were analyzed and used to predict the QTLs in a "one trait to one marker" model, in which for all markers that constructed the linkage maps, each trait was tested independently against each one of the markers. In the provided examples, altogether nine markers were found to be related to traits associated with oil and/or yield components (see Table 1 above), with one marker common to all high oil and/or high yield populations. The occurrence of high oil and/or high yield level markers in two or more linkage maps of the F2 population (repetitive markers) strengthened its significance as representative for high protein level QTL.

In general, the six linkage F2 populations presented different markers that related to high oil and/or high yield levels. However, subsets of common markers were found to be shared by multiple populations and are referred to herein as marker cassettes.

It is emphasized that the breeding process is explained using non-limiting examples from a specific part of the breeding program, and is not limited to the specific populations and varieties derived by this specific part of the breeding program. For example, different F2 population may be bred and used to derive additional varieties that are characterized by one or more of the disclosed QTLs.

Following TPGC Discovery (iii), an in-silico breeding program (iv) was established to process the TPGC blend (including combinations of QTLs for different plants) to simulate and predict the genotypic states of self, cross-self and hybrid plant with respect to the QTLs and their predicted effects on each phase of the markers for the high oil and/or high yield level trait. The in-silico breeding program was constructed to yield millions of in silico selfing combinations which were bred and evaluated in-silico up to F8—to measure the potential for each of the genotyped plants to acquire the high oil and/or high yield level in the right combination at the right phase. The analysis resulted in identifying ca. 300 F2 plants having the highest score for high oil and/or high yield level, which were thus chosen for the actual selfing and cross-selfing procedures. The F3 seeds from these selected F2 plants were sown in plots in the subsequent growing season. Under this procedure, QTLs from different populations were combined to yield F3 plants containing new and unique cassettes of QTLs and resulting in high oil and/or high yield levels.

The high oil and/or high yield sesame lines were then validated as retaining the trait in the following generations by genotyping the F3 and some subsequent generation offspring to verify they maintained the identified marker cassettes. Specifically, the parental lines of linkage F2 populations together with 300 different sesame cultivars (landraces and old commercial varieties) were genotyped based on high oil and/or high yield level markers of all populations. The cassettes detailed in Table 1 were found to wholly differentiate the developed high oil and/or high yield lines from the rest of the sesame cultivars screened.

Figure 3:
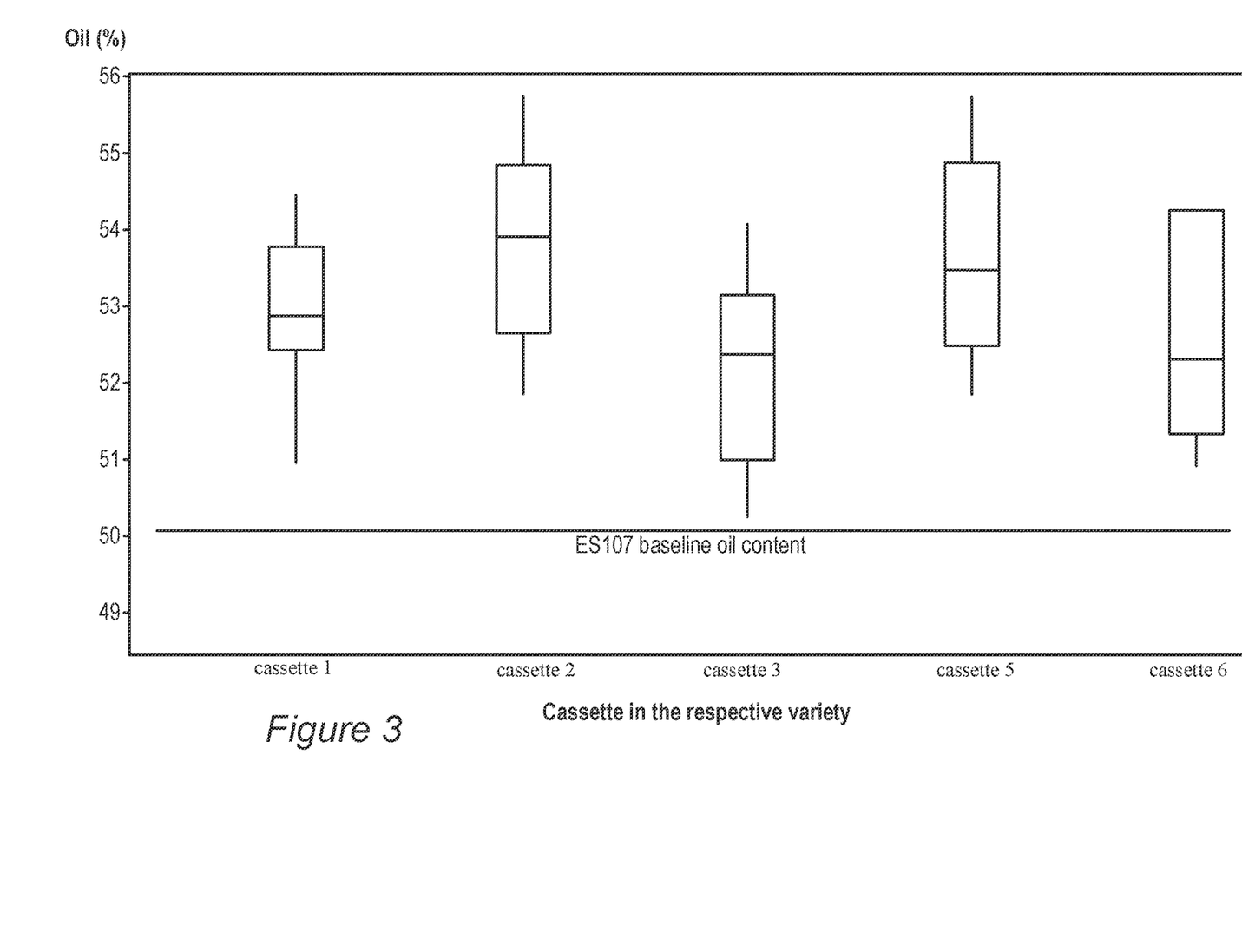
FIG. 3 provides comparisons of the levels of oil in disclosed varieties, according to some embodiments of the invention, with respect to a previous variety (ES107).
Figure 4:
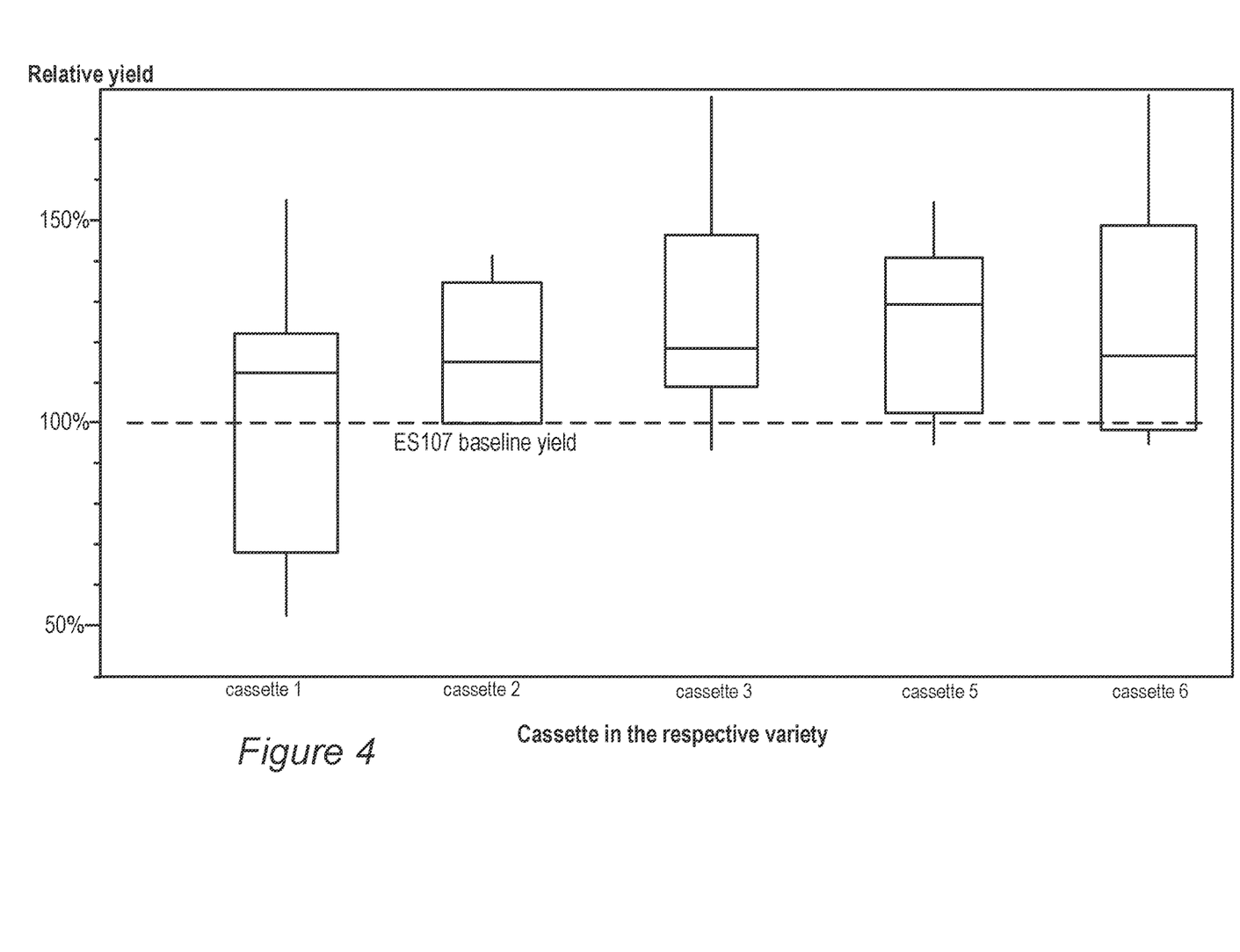
FIG. 4 provides comparisons of the levels of yield in disclosed varieties, according to some embodiments of the invention, with respect to a previous variety (ES107).

FIGS. 3 and 4 provide comparisons of the levels of oil and yield in disclosed varieties, according to some embodiments of the invention, with respect to a previous variety, sesame variety ES107 (which is a registered line lacking the disclosed cassettes). As illustrated in FIG. 3, compared to an oil level of 50% in sesame variety ES107, disclosed varieties exhibit oil levels that range between 52-54%, and even reaching above 55% in some measurements. Accordingly, disclosed varieties exhibit relative increases of 4% and up to 10% in the oil level compared to ES107. As illustrated in FIG. 4, compared to a baseline yield level denoted as 1 (100%) in sesame variety ES107, disclosed varieties exhibit yield levels that range between 10-30% above the yield level of prior art varieties. Accordingly, most disclosed varieties exhibit relative increases of at least 15% in yield with respect to prior art varieties.

The inventors note that none of the high oil and/or high yield sesame plants with shatter-resistant capsules that were bred according to the methods described herein is naturally occurring; indeed, they were derived by highly complicated computationally-supported breeding methods 200 described above, in which the genotypes of multiple sesame varieties were judiciously combined and analyzed, to discover and accumulate the recited QTL markers and corresponding phenotypic traits. Although the recited sesame plants are not genetically modified by sequences originating from other species, they cannot be reached merely by natural processes, as is evident by the detailed and intentional breeding program that was applied to specifically measure required characteristics, detect corresponding markers using bioinformatics methods and combine the detected QTLs in the selected varieties by classic breeding approaches. The inventors note that due to the huge complexity of the breeding program, involving growing, selecting and breeding of hundreds of varieties over many generations in the field, and based on genetic analysis of the varieties and of the relations of markers to phenotypic characteristics, this breeding process cannot happen merely by natural means and therefore cannot be considered a natural phenomenon. It is further noted that due to the shatter-resistance characteristics, disclosed varieties are severely hindered from natural plant propagation. Finally, it is noted that while the disclosed QTL markers are not heterologous to sesame as a species, the identified QTLs are not present in the recited combinations in any of over 200 prior art varieties which were used as initial breeding stock, and that the QTLs genomics of the sesame plants has been significantly and judiciously modified by the breeding program. Therefore, at the taxonomic level of the varieties, the high oil and/or high yield sesame plants may be considered hybridized in that the QTL markers are mixed and introduced from other sesame varieties.

In the above description, an embodiment is an example or implementation of the invention. The various appearances of "one embodiment", "an embodiment", "certain embodiments" or "some embodiments" do not necessarily all refer to the same embodiments. Although various features of the invention may be described in the context of a single embodiment, the features may also be provided separately or in any suitable combination. Conversely, although the invention may be described herein in the context of separate embodiments for clarity, the invention may also be implemented in a single embodiment. Certain embodiments of the invention may include features from different embodiments disclosed above, and certain embodiments may incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some embodiments. Other possible variations, modifications, and applications are also within the scope of the invention. Accordingly, the scope of the invention should not be limited by what has thus far been described, but by the appended claims and their legal equivalents.

What is claimed is:

1. A high oil and/or high yield sesame plant, progeny thereof or part thereof with shatter-resistant capsules, the sesame plant, progeny thereof or part thereof comprising:

a plurality of quantitative trait loci (QTLs) linked to a corresponding plurality of nucleic acid genetic markers that are associated with a plurality of phenotypic traits of the sesame plant comprising at least an oil level trait and a yield trait, wherein the phenotypic traits comprise at least a 1% increase in oil content and/or at least a 15% increase in yield compared to lines not expressing any of the QTLs, wherein the QTLs are combined from a plurality of sesame varieties by computationally supported breeding, wherein the QTLs comprise QTL 1 linked to a genetic marker at position 9215531 on sesame chromosome 5, wherein the genetic marker is associated with high oil content, and the sesame plant, progeny thereof or part thereof is homozygous with respect to the genetic marker, wherein the genetic marker has the nucleic acid sequence set forth in SEQ ID NO: 1, and wherein the sesame plant, progeny thereof or part thereof further comprises at least one of: QTLs 2, 3; QTLs 2, 3, 4, 5; QTLs 2, 3, 4, 5, 7; QTLs 3, 8, 9; or QTLs 3, 4, 6, 8, 9; wherein:

QTL 2 linked to genetic markers at position 13724834 on sesame chromosome 12, wherein the genetic markers are associated with high oil content and have the nucleic acid sequence set forth in SEQ ID NO: 3 or 4, QTL 3 linked to genetic markers at position 7267144 on sesame chromosome 13, wherein the genetic markers are associated with high yield and have the nucleic acid sequence set forth in SEO ID NO: 5 or 6, QTL 4 linked to genetic markers at position 15457227 on sesame chromosome 8, wherein the genetic markers are associated with high oil content and have the nucleic acid sequence set forth in SEQ ID NO: 7 or 8, QTL 5 linked to genetic markers at position 19580227 on sesame chromosome 6, wherein the genetic markers are associated with high oil content and have the nucleic acid sequence set forth in SEQ ID NO: 9 or 10, QTL 6 linked to genetic markers at position 18811179 on sesame chromosome 6, wherein the genetic markers are associated with high yield and have the nucleic acid sequence set forth in SEQ ID NO: 11 or 12, QTL 7 linked to genetic markers at position 471385 on sesame chromosome 6, wherein the genetic markers are associated with high oil content and have the nucleic acid sequence set forth in SEQ ID NO: 13 or 14, QTL 8 linked to genetic markers at position 18953887 on sesame chromosome 9, wherein the genetic markers are associated with high yield and have the nucleic acid sequence set forth in SEQ ID NO: 15 or 16, and QTL 9 linked to genetic markers at position 19270856 on sesame chromosome 1, wherein the genetic markers are associated with high yield and have the nucleic acid sequence set forth in SEQ ID NO: 17 or 18.

2. The high oil and/or high yield sesame plant, progeny thereof or part thereof with shatter-resistant capsules, according to claim 1, wherein the sesame plant, progeny thereof or part thereof further comprises:

QTL 2, wherein the sesame plant, progeny thereof or part thereof is homozygous with respect to SEQ ID NO: 3, and QTL 3, wherein the sesame plant, progeny thereof or part thereof is homozygous with respect to SEQ ID NO: 6.

3. The high oil and/or high yield sesame plant, progeny thereof or part thereof with shatter-resistant capsules, according to claim 1, wherein the sesame plant, progeny thereof or part thereof further comprises:

QTL 2, wherein the sesame plant, progeny thereof or part thereof is homozygous or heterozygous with respect to SEQ ID NO: 4, QTL 3, wherein the sesame plant, progeny thereof or part thereof is homozygous with respect to SEQ ID NO: 6, and QTL 4, wherein the sesame plant, progeny thereof or part thereof is homozygous with respect to SEQ ID NO: 7.

4. The high oil and/or high yield sesame plant, progeny thereof or part thereof with shatter-resistant capsules, according to claim 3, wherein the sesame plant, progeny thereof or part thereof further comprises:

QTL 5, wherein the sesame plant, progeny thereof or part thereof is homozygous or heterozygous with respect to SEQ ID NO: 10.

5. The high oil and/or high yield sesame plant, progeny thereof or part thereof with shatter-resistant capsules according to claim 3, wherein the sesame plant, progeny thereof or part thereof further comprises:

QTL 5, wherein the sesame plant, progeny thereof or part thereof is homozygous with respect to SEQ ID NO: 9, and QTL 7, wherein the sesame plant, progeny thereof or part thereof is homozygous or heterozygous with respect to SEQ ID NO: 13.

6. The high oil and/or high yield sesame plant, progeny thereof or part thereof with shatter-resistant capsules according to claim 1, wherein the sesame plant, progeny thereof or part thereof further comprises:

QTL 2, wherein the sesame plant, progeny thereof or part thereof is homozygous or heterozygous with respect to SEQ ID NO: 4, QTL 3, wherein the sesame plant, progeny thereof or part thereof is homozygous or heterozygous with respect to SEQ ID NO: 6, QTL 4, wherein the sesame plant, progeny thereof or part thereof is homozygous or heterozygous with respect to SEQ ID NO: 7, QTL 5, wherein the sesame plant, progeny thereof or part thereof is homozygous or heterozygous with respect to SEQ ID NO: 10, and QTL 6, wherein the sesame plant, progeny thereof or part thereof is homozygous or heterozygous with respect to SEQ ID NO: 11.

7. The high oil and/or high yield sesame plant, progeny thereof or part thereof with shatter-resistant capsules according to claim 1, wherein the sesame plant, progeny thereof or part thereof further comprises:

QTL, 8 wherein the sesame plant, progeny thereof or part thereof is homozygous with respect to SEQ ID NO: 15, and QTL 9, wherein the sesame plant, progeny thereof or part thereof is homozygous or heterozygous with respect to SEQ ID NO: 17.

8. The high oil and/or high yield sesame plant, progeny thereof or part thereof with shatter-resistant capsules according to claim 7, wherein the sesame plant, progeny thereof or part thereof further comprises:

QTL 3, wherein the sesame plant, progeny thereof or part thereof is homozygous with respect to SEQ ID NO: 6.

9. The high oil and/or high yield sesame plant, progeny thereof or part thereof with shatter-resistant capsules according to claim 7, wherein the sesame plant, progeny thereof or part thereof further comprises:

QTL 3, wherein the sesame plant, progeny thereof or part thereof is homozygous or heterozygous with respect to SEQ ID NO: 5, QTL 4, wherein the sesame plant, progeny thereof or part thereof is homozygous or heterozygous with respect to SEQ ID NO: 7, and QTL 6, wherein the sesame plant, progeny thereof or part thereof is homozygous or heterozygous with respect to SEQ ID NO: 11.

10. The high oil and/or high yield sesame plant, progeny thereof, or part thereof with shatter-resistant capsules according to claim 1, wherein the part thereof comprises any of: a seed, an endosperm, an ovule, pollen, cell, cell culture, tissue culture, plant organ, protoplast, meristem, embryo, or a combination thereof.

* * * * *